(12) United States Patent
Li et al.

(10) Patent No.: US 9,604,966 B2
(45) Date of Patent: Mar. 28, 2017

(54) CRIZOTINIB PREPARATION METHOD

(71) Applicant: Zhejiang Jiuzhou Pharmaceutical Co., Ltd., Taizhou (CN)

(72) Inventors: Yuanqiang Li, Taizhou (CN); Jianqiang Qian, Taizhou (CN); Daqing Che, Taizhou (CN)

(73) Assignee: Zhejiang Jiuzhou Pharmaceutical Co., Ltd, Taizhou, Zhejiang (CN)

( * ) Notice: Subject to any disclaimer, the term of this patent is extended or adjusted under 35 U.S.C. 154(b) by 0 days.

(21) Appl. No.: 14/647,450

(22) PCT Filed: Feb. 13, 2014

(86) PCT No.: PCT/CN2014/072038
§ 371 (c)(1),
(2) Date: May 27, 2015

(87) PCT Pub. No.: WO2014/124594
PCT Pub. Date: Aug. 21, 2014

(65) Prior Publication Data
US 2015/0307476 A1    Oct. 29, 2015

(30) Foreign Application Priority Data
Feb. 16, 2013   (CN) .......................... 2013 1 0051483

(51) Int. Cl.
*C07D 401/14* (2006.01)
*C07D 403/02* (2006.01)
*C07D 213/75* (2006.01)

(52) U.S. Cl.
CPC ......... *C07D 401/14* (2013.01); *C07D 213/75* (2013.01)

(58) Field of Classification Search
CPC ...................... C07D 403/02; C07D 401/14
USPC .............. 514/318, 341; 546/194, 275.4
See application file for complete search history.

(56) References Cited

U.S. PATENT DOCUMENTS

2006/0128724 A1* 6/2006 Cui ...................... C07D 401/14
                                                              514/255.05

FOREIGN PATENT DOCUMENTS

| CN | 101018780 | A | 8/2007 |
|---|---|---|---|
| CN | 101735198 | A | 6/2010 |
| CN | 102850328 | * | 1/2013 |
| CN | 102850328 | A | 1/2013 |
| CN | 103373986 | * | 10/2013 |
| CN | 103373986 | A | 10/2013 |

OTHER PUBLICATIONS

ChemPep "Overview of peptide . . . " p. 1-5 (2005).*

Jasperse "Chem 360 notes . . . " p. 1-26 (2007).*
Bienert et al. "Synthesis and . . . " J. Label. Compounds and Radiopharm. v.27(12)1401-1409 (1990).*
English abstract; China patent application No. CN103373986A, (2013).
English abstract; China patent application No. CN101735198A, (2009).
Patent family of CN101018780A, (2007).
English abstract; China patent application No. CN102850328A, (2011).

* cited by examiner

*Primary Examiner* — Celia Chang

(57) ABSTRACT

The present invention relates to the technical field of medicine and organic synthesis, particularly to a method for preparing crizotinib. The method comprises the compound of formula b and the compound of formula e undergoing Suzuki coupling reaction to produce the compound of formula a which then was subjected to deprotection to afford (±) crizotinib.

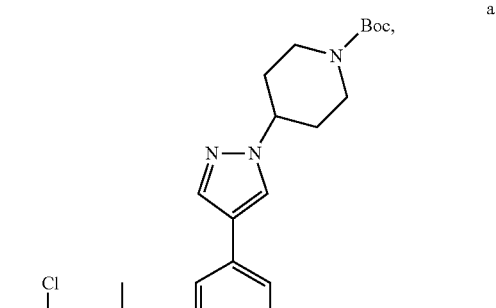

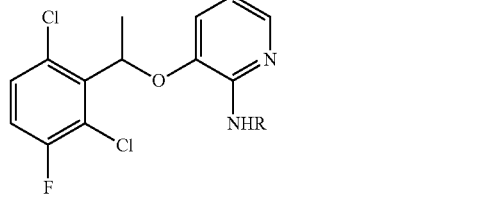

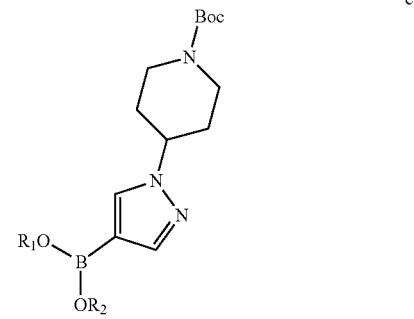

10 Claims, 1 Drawing Sheet

CRIZOTINIB PREPARATION METHOD

This application claims the priority of China Patent Application No. 201310051483.3, filed with the Patent Office of China on Feb. 16, 2013, titled "Crizotinib Preparation Method", the contents of which are incorporated herein by reference in its entirety.

FIELD OF THE INVENTION

The present invention relates to the technical field of medicine and organic synthesis, particularly to a method for preparing crizotinib.

BACKGROUND OF THE INVENTION

Crizotinib, a new drug developed by Pfizer to treat lung cancer, is one of the first targeted therapy in the treatment of anaplastic lymphoma kinase (ALK), active in ALK-positive locally advanced or metastaticnon-small cell lung cancer and it is described chemically as 3-(R)-[1-(2,6-dichloro-3-fluorophenyl)ethoxy]-5-[1-(piperidin-4-yl)-1H-pyrazol-4-yl]pyridin-2-amine.

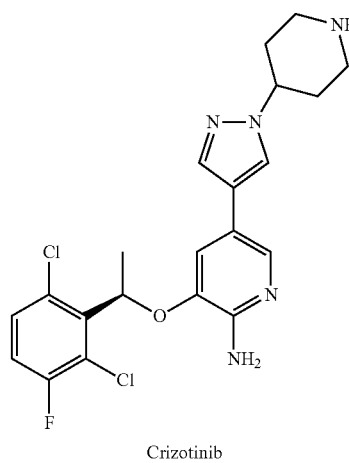

Crizotinib

Currently, the commonly used methods for preparing crizotinib are, for example, as described in America patent application of Pfizer with publication no. US20060128724.

Method 1:

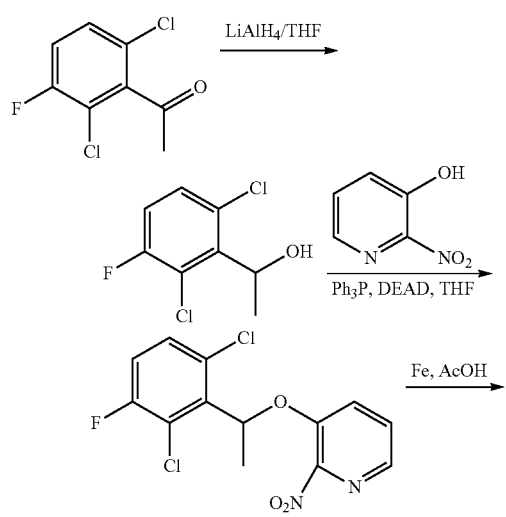

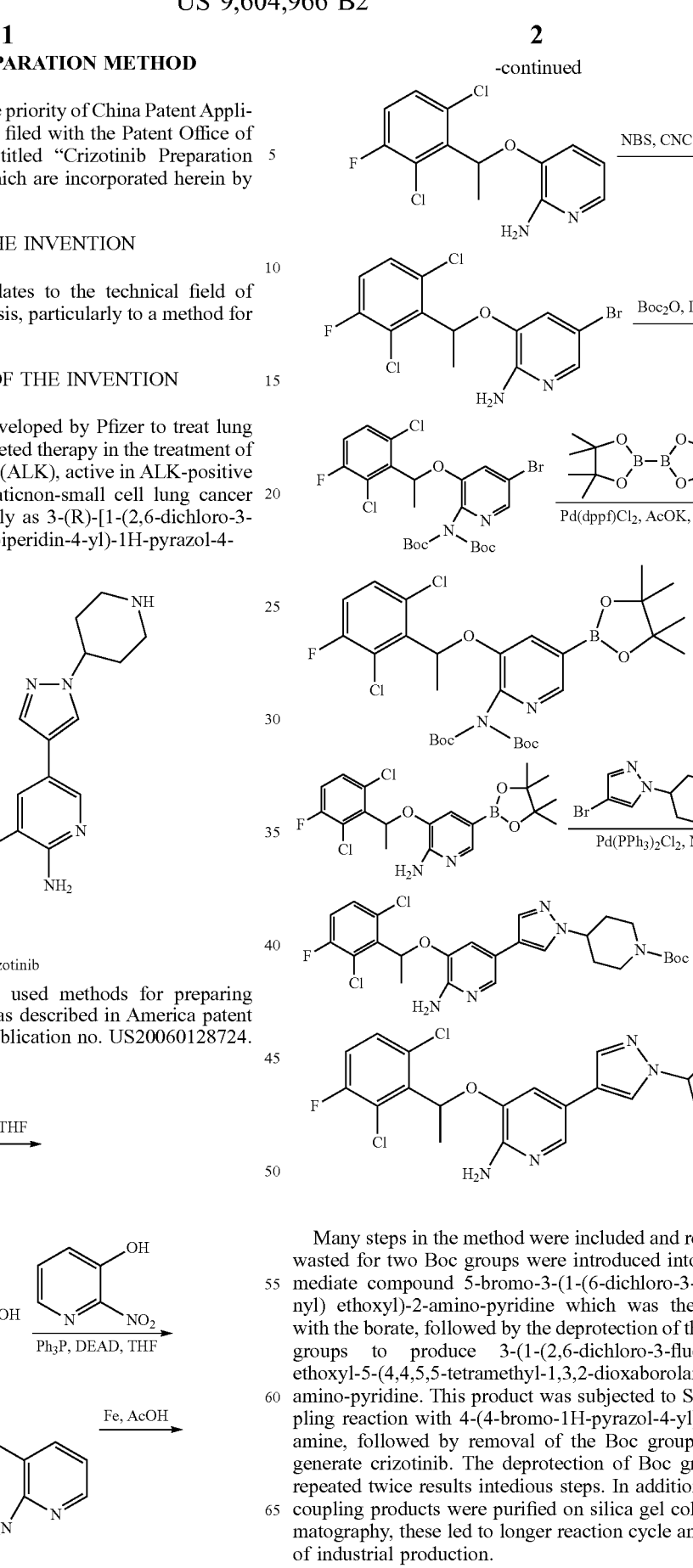

Many steps in the method were included and reagent was wasted for two Boc groups were introduced into the intermediate compound 5-bromo-3-(1-(6-dichloro-3-fluorophenyl) ethoxyl)-2-amino-pyridine which was then coupled with the borate, followed by the deprotection of the two Boc groups to produce 3-(1-(2,6-dichloro-3-fluorophenyl) ethoxyl-5-(4,4,5,5-tetramethyl-1,3,2-dioxaborolan-2-yl)-2-amino-pyridine. This product was subjected to Suzuki coupling reaction with 4-(4-bromo-1H-pyrazol-4-yl)pyridin-2-amine, followed by removal of the Boc group to finally generate crizotinib. The deprotection of Boc group being repeated twice results intedious steps. In addition, both the coupling products were purified on silica gel column chromatography, these led to longer reaction cycle and the limit of industrial production.

Method 2:

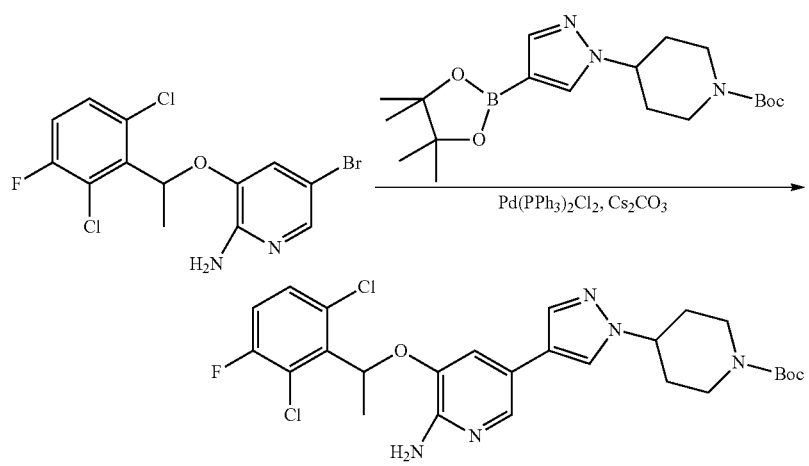

Sodium hydride is difficult to handle and may cause explosion easily in this method.

Method 3:

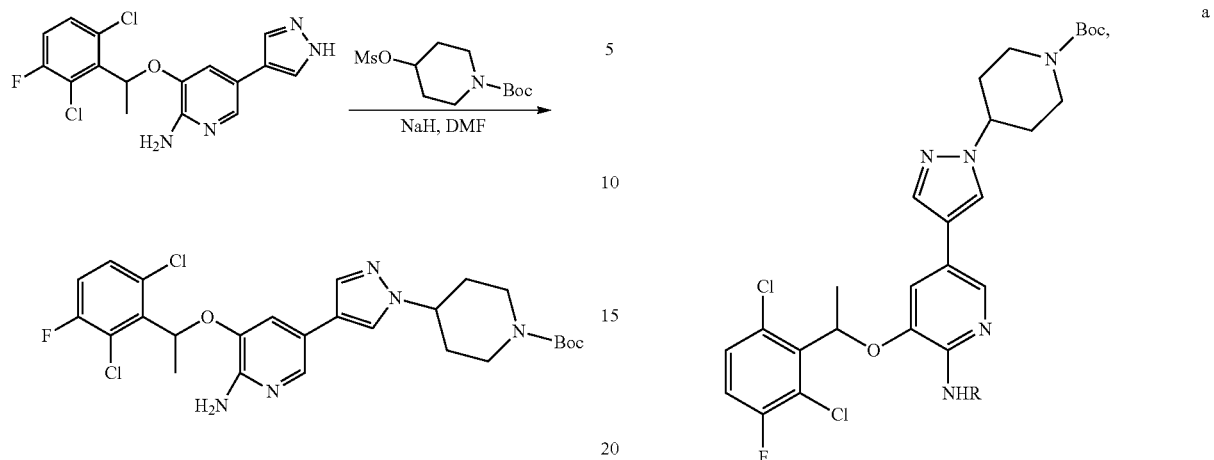

More byproducts were generated in this method, for the free amino group of 5-bromo-3-(2,6-dichloro-3-fluorophenyl)ethoxy)2-amino-pydine wasn't protected. The product was produced in a low yield of 61% after purification on silica gel column chromatography.

SUMMARY OF THE INVENTION

To solve the above-mentioned problems, such as multi-steps, low yield etc., the following methods for preparing crizotinib were provided in the present invention:

A method for preparing the compound of formula a comprises Suzuki coupling reaction of the compound of formula b and the compound of formula e to produce the compound of formula a, -continued

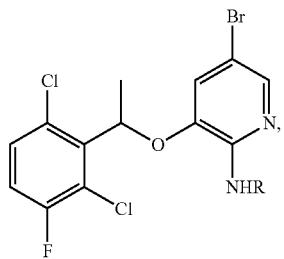

b

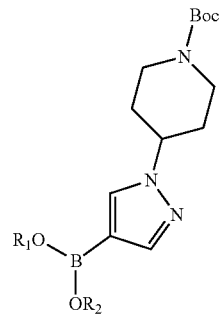

e

Wherein R is an amino-protecting group, particularly is Boc or Cbz.

Both $R_1$ and $R_2$ are hydrogen or methyl, or are incorporated into the group having the following formula M:

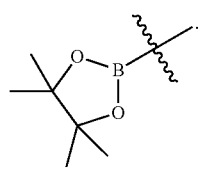

M

The preferred coupling agent employed in the Suzuki coupling reaction is palladium catalyst and base, the palladium catalyst can be $Pd(OAc)_2$, $Ph(Ph_3P)_4$, $Pd(Ph_3P)_2Cl_2$, $Pd(dppf)Cl_2$ or Pd/C and the preferred base can be sodium carbonate, potassium carbonate or cesium carbonate. A skill person in the art can select suitable reaction temperature in accordance with the solvent employed. For example, the temperature is 40-100° C. when the solvent is dimethylformamide.

Further, the compound of formula a was subjected to deprotection of Boc to afford (±) crizotinib. The agent employed in the deprotection is hydrochloric acid-alcohol solution, preferably, is hydrochloric acid-methanol solution or hydrochloric acid-ethanol solution.

The compound of formula b can be obtained by the Mitsunobu reaction of the compound of formula b and the compound of formula f to generate the compound of formula b,

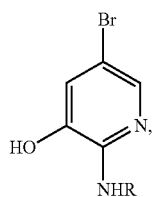

c

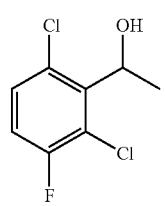

f

Wherein, R is protecting group, preferably, is Boc or Cbz.

The agent employed can be diethyl azodicarboxylate (DEAD), diisopropylazodicarboxylate (DIAD) or azodicarbonyldipiperidine (ADDP) and triphenylphosphine or tri-n-butylphosphine. A skill person in the art can select suitable reaction temperature in accordance with the solvent employed. For example the temperature is 0-40° C. when the solvent is tetrahydrofuran.

The compound of formula c is generated by protecting the amino-group of the compound of formula d,

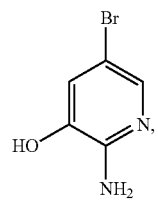

d

The preferred protecting agent employed is di-tert-butyl dicarbonate ($Boc_2O$) or benzyloxycarbonyl chloride (CbzCl). A skill person in the art can select suitable reaction temperature in accordance with the solvent employed. For example the reaction can be carried out at room temperature when the solvent is dichloromethane.

Further, the preferred compound of formula a has the following formula a',

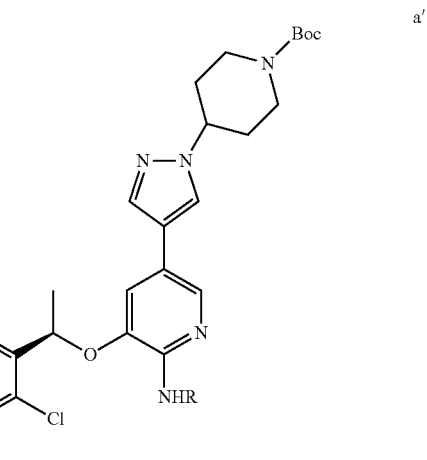

a'

The said compound further undergoes the deprotection to afford crizotinib.

The compound of formula a' can be produced from the compound of formula f',

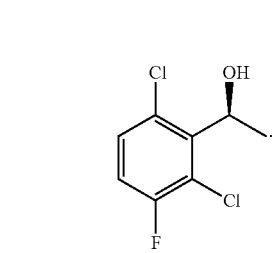

f'

The present invention provides a method for preparing crizotinib, which has the following advantages: the reaction route is short. Only one amino protecting group was introduced into the compound of formula d, thus saving the agents and benefit to environment protection. After the completion of the Mitsunobu reaction, the product can be produced in desired purify by utilizing ethanol recrystallization instead of the silica gel column chromatography purification. After the completion of the Suzuki coupling reaction, the yield is over 90% without the purification on silica gel column chromatography, which was increased at least by 25% as compared with that of 65% in the prior art. The deprotection step was only once performed in the last step of all the processes. Thus, the reaction processes are shortened and the deprotection step was carried out in the presence of hydrochloric acid-alcohol solution, which can increase the purity of crizotinib.

The following abbreviations have been used in the present invention:

Boc: t-butyloxycarboryl;
Cbz: carbobenzyloxy;
DEAD: diethyl azodicarboxylate;
DMAP: 4-diMethylaMinopyridine;
Mitsunobu reaction: the Mitsunobu reaction is a type of bimolecular nucleophilicsubstitution ($S_N2$ reaction).

Suzuki coupling reaction: is also referred to as the "Suzuki Coupling, which is Palladium-catalyzed cross-coupling reaction of arylboronic acid, alkenylboronic acid or esters thereof with aryl halides or alkene, wherein, halide is selected from chloride, bromide, iodide.

DETAILED EMBODIMENTS

Figure 1:
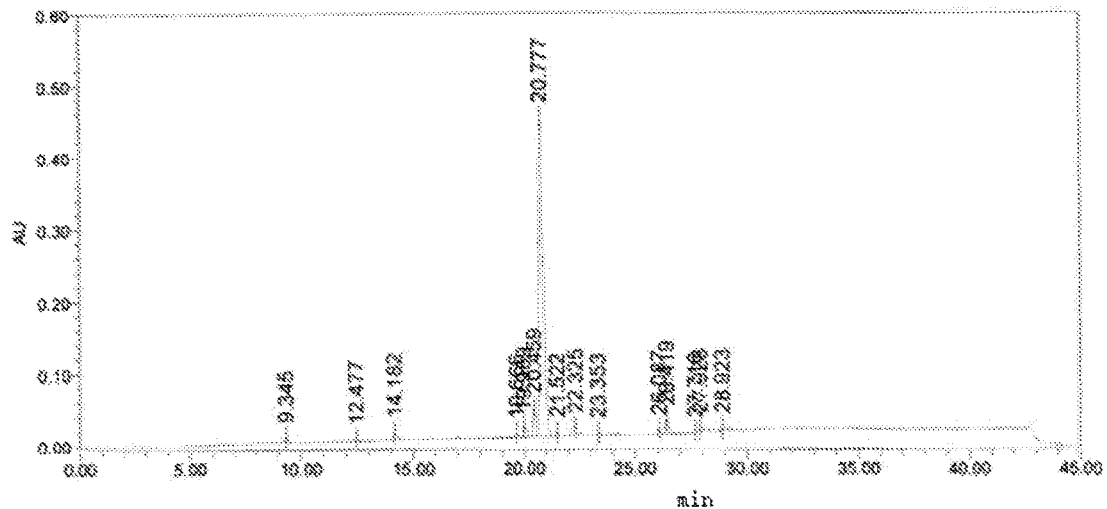
FIG. 1 is HPLC spectrogram of reaction mixture produced in comparison example 1.
Figure 2:
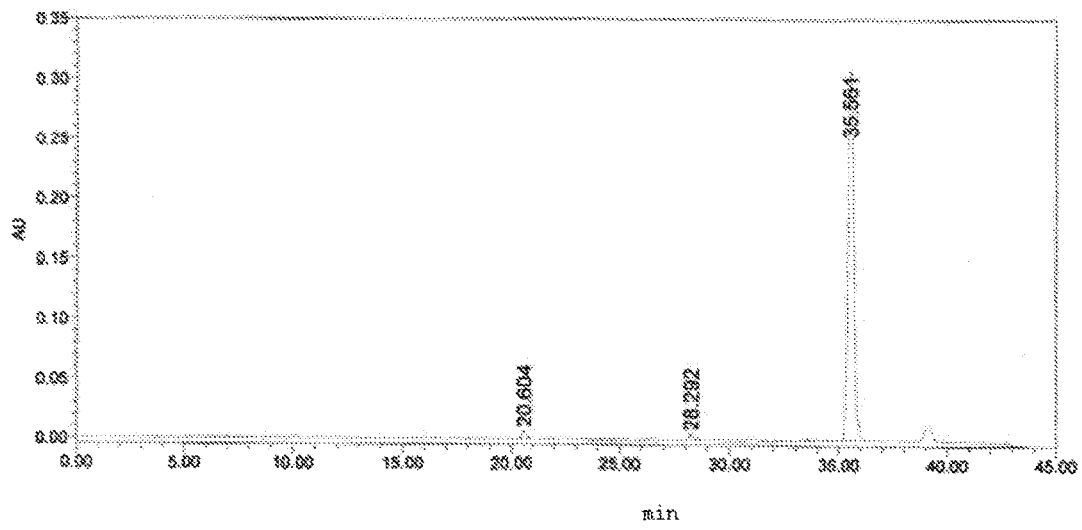
FIG. 2 is HPLC spectrogram of reaction mixture produced in example 3.

In order to better understand the present invention, it is illustrated in detail by the following examples. However, it should be understood that these descriptions are not to limit the claims of the present invention.

Comparison Example 1

The preparation of 3-(1-(2,6-dichloro-3-fluorophenyl)ethoxy)-5-(1-(1-tert-butyloxycarbonyl-piperid-4-yl)-1H-pyrazol-4-yl)-2-amino-pyridine The following step was performed according to the method described in US20060128724 (see page 70 paragraph[0433]).

be produced in 79.36% yield by HPLC analysis of the reaction mixture. The data analyzed by HPLC was presented in table 1.

TABLE 1

| | the data analyzed by HPLC | | | |
|---|---|---|---|---|
| No. | RT (min) | Area (mV*sec) | Height (mV) | Area (Percent) |
| 1 | 9.345 | 53698 | 7138 | 0.73 |
| 2 | 12.477 | 34044 | 2873 | 0.46 |
| 3 | 14.182 | 119399 | 11074 | 1.62 |
| 4 | 19.666 | 50648 | 5804 | 0.69 |
| 5 | 19.989 | 142140 | 15065 | 1.92 |
| 6 | 20.459 | 420142 | 40378 | 5.68 |
| 7 | 20.777 | 5866747 | 442507 | 79.36 |
| 8 | 21.522 | 62059 | 6279 | 0.84 |
| 9 | 22.325 | 160437 | 10263 | 2.17 |
| 10 | 23.353 | 35789 | 3174 | 0.48 |
| 11 | 26.087 | 68718 | 6233 | 0.93 |
| 12 | 26.419 | 243154 | 1907 | 3.29 |
| 13 | 27.716 | 9133 | 1479 | 0.12 |
| 14 | 27.928 | 52481 | 5260 | 0.71 |
| 15 | 28.923 | 74358 | 4089 | 1.01 |

Example 1

The preparation of 5-bromo-3-hydroxy-2-tert-butyloxycarbonylamino pyridine

To a solution of 2-amino-3-hydroxy-5-bromopyridine (10.0 g, 53.0 mmol) and $Et_3N$ (10 mL, 71.8 mmol) in dichloromethane (100 mL) was added $Boc_2O$ (12.7 g, 58.4 mmol). The mixture was stirred at room temperature for 18 h and continued to stir for 30 min after the addition of 150 ml water. The reaction mixture was filtrated off through celite. The organic layer was separated and the aqueous layer was extracted with 150 dichloromethane. The combined organic layers were washed with saturated NaCl aqueous solution (2×100 mL) and then dried over anhydrous $Na_2SO_4$. The solvent was removed under reduced pressure and the obtained residue was triturated in hexane (100 mL),

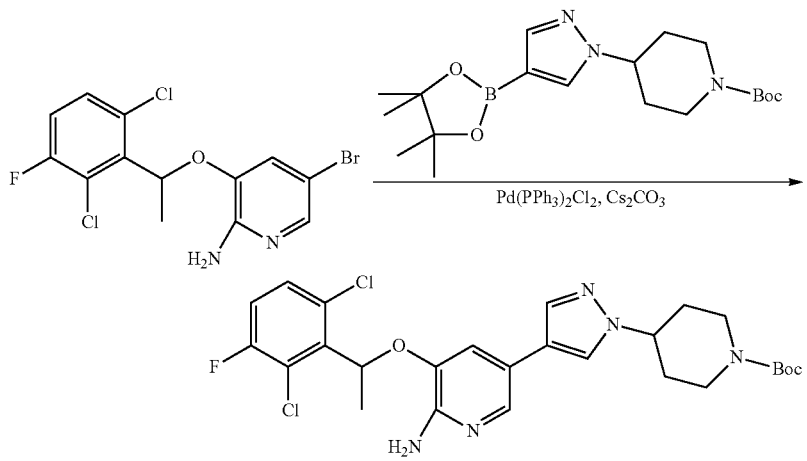

After completion of the reaction, 3-(1-(2,6-dichloro-3-fluorophenyl)ethoxy)-5-(1-(1-tert-butyloxycarbonyl-piperid-4-yl)-1H-pyrazol-4-y)-2-amino-pyridine was found to filtrated, and dried under vacuum to afford 15.0 g 5-bromo-3-hydroxy-2-tert-butyloxycarbonylamino pyridine as a white solid, with a yield of 98.0%.

¹H NMR (400 MHz, CDCl₃): δ 7.98 (d, J=2.0 Hz, 1H), 7.58 (d, J=2.0 Hz, 1H), 4.67 (brs, 2H), 1.56 (s, 9H); ¹C NMR (100 MHz, CDCl₃): δ 150.4, 150.1, 145.3, 133.5, 131.5, 106.5, 85.0, 27.6.

Example 2

The preparation of 5-bromo-3-(1-(2,6-dichloro-3-fluorophenyl)ethoxy)-2-tert-butyloxycarbonylamino pyridine 1-(2,6-dichloro-3-fluorophenyl)ethanol (1.0 g, 4.78 mmol), 5-bromo-3-hydroxy-2-tert-butyloxycarbonyl amino pyridine (1.4 g, 4.78 mmol) and triphenylphosphine (1.6 g, 6.2 mmol) were dissolved in 20 ml of anhydrous THF under N₂ atmosphere. The reaction mixture was cooled to below 0° C. and then diisopropylazodiformate (1.25 g, 6.2 mmol) was added to the mixture at below 5° C. The mixture was stirred at room temperature for 6 h, and then was filtered. The solvent was evaporated under reduced pressure to afford product as an oil, which was then recrystallized by ethanol to produce 2.13 g of 5-bromo-3-(1-(2,6-dichloro-3-fluorophenyl)ethoxy)-2-tert-butyloxycarbonylamino pyridine as a white solid with a yield of 93.0%.

¹H NMR (400 MHz, CDCl₃): δ 8.05 (d, J=1.6 Hz, 1H), 7.51 (brs, 1H), 7.32 (dd, J=4.8 Hz, 4.4 Hz, 1H), 7.12-7.08 (m, 2H), 6.05 (q, J=6.4 Hz, 1H), 1.85 (d, J=6.4 Hz, 3H), 1.55 (s, 9H);

Example 3

The preparation of 3-(1-(2,6-dichloro-3-fluorophenyl)ethoxy)-5-(1-(1-tert-butyloxycarbonylaminopiperid-4-yl)-1H-pyrazol-4-yl)-2-tert-butyloxycarbonylamino-pyridine 5-bromo-3-(1-(2,6-dichloro-3-fluorophenyl)-ethoxy)-2-tert-butyloxycarbonylamino-pyridine (0.24 g, 0.5 mmol) and 4-(4-(4,4,5,5-tetramethyl-1,3,2-dioxaborolan-2-yl)-1H-pyrazol-1-yl)-1-tert-butyloxycarbonyl pyridine (0.19 g, 0.5 mmol) were dissolved in 5 ml of DMF, and then an aqueous solution of Na₂CO₃ (0.16 g, 1.5 mmol) in 1 ml water and Pd(Ph₃P)₂Cl₂ (8.8 mg, 0.0125 mmol) were added successively. After being heated to 60° C. with stirring for 6 h under N₂ atmosphere, the mixture was cooled to room temperature, filtrated to remove undissolved solid, and extracted with methyl tert-butyl ether (3×5 mL). Combined organic layers were washed with saturated NaCl aqueous solution (2×5 mL), dried over anhydrous Na₂SO₄ and the solvent was evaporated up to dryness under reduced pressure to afford 3-(1-(2,6-dichloro-3-fluorophenyl)ethoxy)-5-(1-(1-tert-butyloxycarbonylaminopiperid-4-yl)-1H-pyrazol-4-yl)-2-tert-butyloxycarbonylamino-pyridine as a white solid, with a yield of 92.3%.

¹H NMR (400 MHz, CDCl₃): δ 8.11 (d, J=1.6 Hz, 1H), 7.61 (s, 1H), 7.56 (s, 1H), 7.51 (s, 1H), 7.30 (dd, J=4.8 Hz, 4.0 Hz, 1H), 7.09-7.05 (m, 2H), 6.13 (q, J=6.8 Hz, 1H), 4.30-4.23 (m, 3H), 2.93-2.87 (m, 2H), 2.15-2.12 (m, 2H), 1.99-1.92 (m, 2H), 1.89 (d, J=6.8 Hz, 3H), 1.56 (s, 9H), 1.48 (s, 9H)

Example 4

The Preparation of (±) Crizotinib 3-(1-(2,6-dichloro-3-fluorophenyl)ethoxy)-5-(1-(1-tert-butyloxycarbonylaminopiperid-4-yl)-1H-pyrazol-4-yl)-2-tert-butyloxycarbonylamino-pyridine (162.6 mg, 0.25 mmol) was dissolved in 2 ml dichloromethane and then the mixture was cooled to below 0° C. After the addition of 0.4 ml hydrochloric acid-ethanol solution, the mixture was stirred at room temperature for 12 h, quenched with 1 ml water, adjusted to pH>9 with 2N NaOH aqueous solution, and then was extracted with dichloromethane (2×10 mL). The combined organic layer was washed with 10 ml saturated NaCl aqueous solution, dried over anhydrous Na₂SO₄ and then evaporated to produce 0.11 g of crizotinib as an off-white solid, with a yield of 97.8%.

Example 5

The preparation of (R)-5-bromo-3-(1-(2,6-dichloro-3-fluorophenyl)ethoxy)-2-tert-butyloxycarbonylamino-pyridine (S)-1-(2,6-dichloro-3-fluorophenyl)ethanol (1.0 g, 4.78 mmol, ee 99.9%), 5-bromo-3-bromo-3-hydroxyl-tert-butyloxycarbonylamino pyridine (1.4 g, 4.78 mmol) and triphenylphosphine (1.6 g, 6.2 mmol) were dissolved in 20 ml of anhydrous THF under N₂ atmosphere, cooled to below 0° C. and then diisopropylazodiformate (1.25 g, 6.2 mmol) was added to the mixture at below 5° C. The mixture was stirred at room temperature for 6 h and then filtered. The solvent was evaporated under reduced pressure to afford product as oil which was recrystallized by ethanol to produce 2.16 g of 5-bromo-3-(1-(2,6-dichloro-3-fluorophenyl)ethoxy)-2-tert-butyloxycarbonylamino pyridine as a white solid with a yield of 94.3%, ee 99.9%.

Example 6

The preparation of (R)-3-(1-(2,6-dichloro-3-fluorophenyl)ethoxy)-5-(1-(1-tert-butyloxycarbonylaminopiperid-4-yl)-1H-pyrazol-4-yl)-2-tert-butyloxycarbonylamino-pyridine (R)-5-bromo-3-(1-(2,6-dichloro-3-fluorophenyl)-ethoxy)-2-tert-butyloxycarbonylamino-pyridine (0.24 g, 0.5 mmol) and 4-(4-(4,4,5,5-tetramethyl-1,3,2-dioxaborolan-2-yl)-1H-pyrazol-1-yl)-1-tert-butyloxycarbonyl pyridine (0.19 g, 0.5 mmol) were dissolved in 5 ml of DMF, then an aqueous solution of Na₂CO₃ (0.16 g, 1.5 mmol) in 1 ml water and Pd(Ph₃P)₂Cl₂ (8.8 mg, 0.0125 mmol) were added successively. After being heated to 60° C. with stirring for 6 h under N₂ atmosphere, the mixture was cooled to room temperature and filtrated to remove undissolved solid. The filtrate was extracted with methyl tert-butyl ether (3×5 mL). The combined organic layer was washed with saturated NaCl aqueous solution (2×5 mL), dried over anhydrous Na₂SO₄ and the solvent was removed under reduced pressure to afford 0.31 g of 3-(1-(2,6-dichloro-3-fluorophenyl)ethoxy)-5-(1-(1-tert-butyloxycarbonylaminopiperid-4-yl)-1H-pyrazol-4-yl)-2-tert-butyloxycarbonylamino-pyridine as a white solid, with a yield of 95.4%, ee 99.9%.

Example 7

The Preparation of Crizotinib (R)-3-(1-(2,6-dichloro-3-fluorophenyl)ethoxy)-5-(1-(1-tert-butyloxycarbonylamino piperid-4-yl)-1H-pyrazol-4-yl)-2-tert-butyloxycarbonylamino-pyridine (162.6 mg, 0.25 mmol) was dissolved in 2 ml dichloromethane and then the mixture was cooled to below 0° C. after the addition of 0.4 ml hydrochloric acid-ethanol solution, the mixture was stirred at room temperature for 12 h, quenched with 1 ml water, adjusted to pH>9 with 2N NaOH aqueous solution, and then was extracted with dichloromethane (2×10 mL). The combined organic layer was washed with 10 ml saturated NaCl aqueous solution, dried over anhydrous $Na_2SO_4$ and then concentrated to produce 0.112 g of crizotinib as an off-white solid, with a yield of 99.6%, ee 99.9%.

Example 8

The preparation of 5-bromo-3-(1-(2,6-dichloro-3-fluorophenyl)ethoxy)-2-tert-butyloxycarbonylamino pyridine 1-(2,6-dichloro-3-fluorophenyl)ethanol (1.0 g, 4.78 mmol), 5-bromo-3-hydroxy-2-tert-butyloxycarbonyl amino pyridine (1.4 g, 4.78 mmol) and triphenylphosphine (1.6 g, 6.2 mmol) were dissolved in 20 ml of anhydrous THF under $N_2$ atmosphere, cooled to below 0° C. and then diisopropylazodiformate (1.08 g, 6.2 mmol) was added to the mixture at below 5° C. The mixture was stirred at room temperature for 6 h, and then was allowed to filtrate. The solvent was removed under reduced pressure to afford product as oil which was recrystallized by ethanol to produce 2.14 g of 5-bromo-3-(1-(2,6-dichloro-3-fluorophenyl)ethoxy)-2-tert-butyloxy carbonylamino pyridine as a white solid with a yield of 93.3%.

Example 9

The preparation of 5-bromo-3-(1-(2,6-dichloro-3-fluorophenyl)ethoxy)-2-benzyloxycarbonyl amino pyridine 1-(2,6-dichloro-3-fluorophenyl)ethanol (1.0 g, 4.78 mmol), 5-bromo-3-hydroxy-2-benzyloxy carbonyl amino pyridine (1.54 g, 4.78 mmol) and triphenylphosphine (1.6 g, 6.2 mmol) were dissolved in 20 ml of anhydrous THF under $N_2$ atmosphere, cooled to below 0° C. and then diisopropylazodiformate (1.25 g, 6.2 mmol) was added to the mixture at below 5° C. The mixture was stirred at room temperature for 6 h, and then was allowed to filtrate. The solvent was removed under reduced pressure to afford product as oil which was recrystallized from ethanol to produce 2.25 g of 5-bromo-3-(1-(2,6-dichloro-3-fluorophenyl)ethoxy)-2-tert-butyloxycarbonylamino pyridine as a white solid with a yield of 91.5%.

Example 10

The preparation of (R)-3-(1-(2,6-dichloro-3-flurophenyl)ethoxy)-5-(1-(1-tert-butyloxycarbonylaminopiperid-4-yl)-1H-pyrazol-4-yl)-2-tert-butyloxycarbonylamino-pyridine 5-bromo-3-(1-(2,6-dichloro-3-fluorophenyl)-ethoxy)-2-tert-butyloxycarbonylamino-pyridine (0.24 g, 0.5 mmol) and 1-(1-tert-butyloxycarbonylamino piperid-4-yl)-1H-pyrazol-4-yl boric acid (0.19 g, 0.5 mmol) were dissolved in 5 ml of DMF, then an aqueous solution of $Na_2CO_3$ (0.16 g, 1.5 mmol) in 1 ml water and $Ph(Ph_3P)_4$ (14.4 mg, 0.0125 mmol) were added successively. After being heated to 60° C. with stirring for 6 h under $N_2$ atmosphere, the mixture was cooled to room temperature, filtrated to remove undissolved solid, extracted with methyl tert-butyl ether (3×5 mL). Combined organic layers were washed with saturated NaCl aqueous solution (2×5 mL), dried over anhydrous $Na_2SO_4$ and the solvent was removed under reduced pressure to afford 0.30 g of 3-(1-(2,6-dichloro-3-fluorophenyl)ethoxy)- 5-(1-(1-tert-butyloxycarbonylaminopiperid-4-yl)-1H-pyrazol-4-yl)-2-tert-butyloxycarbonylamino-pyridine as a white solid, with a yield of 90.1%.

Example 11

The preparation of 3-(1-(2,6-dichloro-3-fluorophenyl)ethoxy)-5-(1-(1-tert-butyloxycarbonylaminopiperid-4-yl)-1H-pyrazol-4-yl)-2-benzyloxycarbonyl amino-pyridine To a solution of 5-bromo-3-(1-(2,6-dichloro-3-fluorophenyl)-ethoxy)-2-benzyloxycarbonyl amino-pyridine (0.24 g, 0.5 mmol) and 4-(4-(4,4,5,5-tetramethyl-1,3,2-dioxaborolan-2-yl)-1H-pyrazol-1-yl)-1-tert-butyloxycarbonyl pyridine (0.19 g, 0.5 mmol) in 5 ml of DMF was added an aqueous solution of $Na_2CO_3$ (0.16 g, 1.5 mmol) in 1 ml water and $Pd(Ph_3P)_2Cl_2$ (8.8 mg, 0.0125 mmol) successively. After being heated to 60° C. with stirring for 6 h under $N_2$ atmosphere, the mixture was cooled to room temperature, filtrated to remove undissolved solid, extracted with methyl tert-butyl ether (3×5 mL). Combined organic layers were washed with saturated NaCl aqueous solution (2×5 mL), dried over anhydrous $Na_2SO_4$ and the solvent was removed under reduced pressure to afford 0.29 g of 3-(1-(2,6-dichloro-3-fluorophenyl) ethoxy)-5-(1-(1-tert-butyloxycarbonylaminopiperid-4-yl)-1H-pyrazol-4-yl)-2-benzyloxycarbonyl amino-pyridine as a white solid, with a yield of 91.8%.

Example 12

The Preparation of (±) Crizotinib

To a solution of 3-(1-(2,6-dichloro-3-fluorophenyl) ethoxy)-5-(1-(1-tert-butyloxycarbonyl aminopiperid-4-yl)-1H-pyrazol-4-yl)-2-tert-butyloxycarbonylamino-pyridine (171 mg, 0.25 mmol) in 2 ml ethanol was added 0.1 g Pd/C and then was stirred at room temperature for 3 h. after completion of the reaction, the reaction mixture was filtrated through celite. The filtrate was concentrated and was extracted with dichloromethane (2×10 mL). The combined organic layer was washed with 10 ml saturated NaCl aqueous solution, dried over anhydrous $Na_2SO_4$ and then concentrated to produce 0.112 g of crizotinib as an off-white solid, with a yield of 99.6%.

The invention claimed is:

1. A method for preparing the compound of formula a, comprising Suzuki coupling reaction of the compound of formula b with the compound of formula e to produce the compound of formula a,

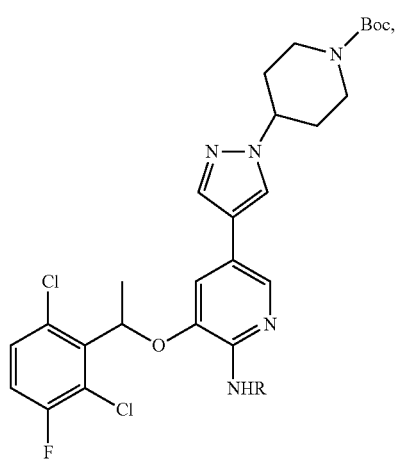

a

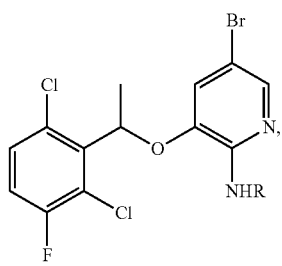

b

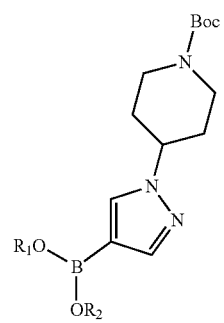

e

Wherein, R is a protecting group, the protecting group is Boc or Cbz;

both $R_1$ and $R_2$ are hydrogen or methyl, or are incorporated into the group having the following formula M:

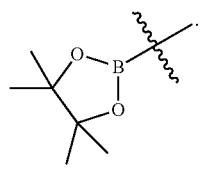

M

2. The method according to claim 1, the agent employed in Suzuki coupling reaction is palladium catalyst and base.

3. The method according to claim 2, the palladium catalyst is $Pd(OAc)_2$, $Ph(Ph_3P)_4$, $Pd(Ph_3P)_2Cl_2$, $Pd(dppf)Cl_2$ or Pd/C; the base is sodium carbonate, potassium carbonate or cesium carbonate.

4. The method according to claim 1, further comprising the reaction of deprotection of the compound of formula a to afford (±) crizotinib.

5. The method according to claim 4, the agent employed in the reaction of deprotection is hydrochloric acid-alcohol solution when the protecting group is Boc, the agent is Pd/C when the protecting group is Cbz.

6. The method according to claim 1, further comprising Mitsunobu reaction of the compound of formula c with the compound of formula f to produce the compound of formula b,

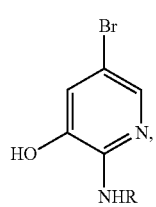

c

7. The method according to claim 6, further comprising the step of protection of the amino-group of the compound of formula d to produce the compound of formula c,

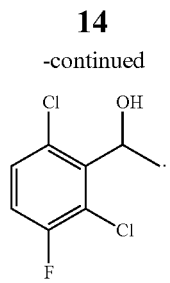

f

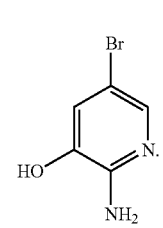

d

8. The method according to claim 7, the protecting agent is di-tert-butyl dicarbonate or benzyloxycarbonyl chloride.

9. The method according to claim 1, the compound of formula a having the structure represented by formula a,

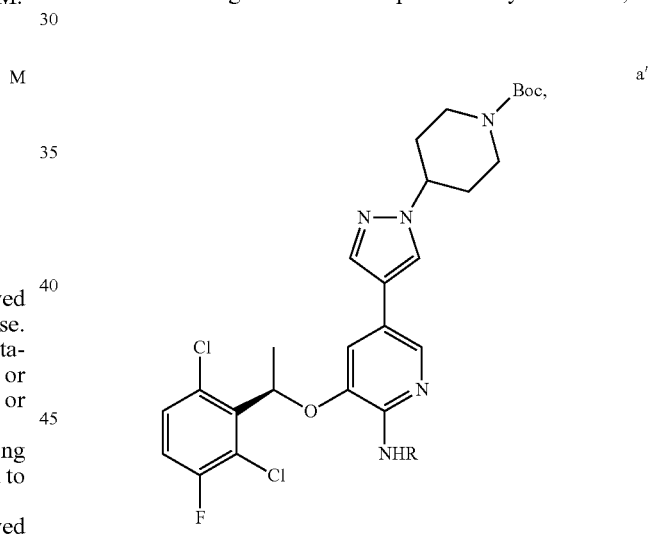

a'

Wherein, R is as defined in claim 1.

10. The method according to claim 9, further comprising the step of converting the compound of formula f' to the compound of formula a',

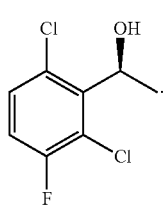

f'

* * * * *